(12) United States Patent
LeMay et al.

(10) Patent No.: US 8,221,375 B2
(45) Date of Patent: Jul. 17, 2012

(54) BARREL FOR A TAMPON APPLICATION ASSEMBLY AND METHODS OF FORMING

(75) Inventors: Jessica Elizabeth LeMay, New York, NY (US); Keith Edgett, Middletown, DE (US); Wayne David Melvin, Camden, DE (US); Kathryn Bennett, Fairfield, CT (US)

(73) Assignee: Playtex Products, Inc., Westport, CT (US)

( * ) Notice: Subject to any disclaimer, the term of this patent is extended or adjusted under 35 U.S.C. 154(b) by 199 days.

(21) Appl. No.: 12/660,969

(22) Filed: Mar. 8, 2010

(65) Prior Publication Data

US 2010/0164139 A1    Jul. 1, 2010

Related U.S. Application Data

(60) Division of application No. 10/619,677, filed on Jul. 15, 2003, now Pat. No. 7,704,242, which is a continuation-in-part of application No. 10/407,159, filed on Apr. 4, 2003, now abandoned.

(51) Int. Cl.
*A61F 13/20* (2006.01)
*A61F 13/15* (2006.01)
*B29C 59/02* (2006.01)
*B29C 59/00* (2006.01)
*B29C 53/00* (2006.01)

(52) U.S. Cl. ............... 604/385.17; 604/385.18; 604/11; 604/15; 604/904; 264/320; 264/293; 156/203; 156/218

(58) Field of Classification Search ............ 604/385.17, 604/385.18, 11, 15, 904; 264/322, 320, 293, 264/296; 83/862; 156/203, 218
See application file for complete search history.

(56) References Cited

U.S. PATENT DOCUMENTS

| | | | |
|---|---|---|---|
| 652,848 A | 7/1900 | Hill | 604/15 |
| 1,171,736 A | 2/1916 | McClanahan | 292/37 |
| 2,476,956 A | 7/1949 | Bonham | 604/15 |
| 2,489,502 A | 11/1949 | Ruth | 604/18 |
| 2,587,717 A | 3/1952 | Fourness | 604/18 |
| D197,751 S | 3/1964 | Rigney et al. | D24/114 |
| 3,139,886 A | 7/1964 | Tallman et al. | 604/12 |
| 3,575,169 A | 4/1971 | Voss et al. | 604/18 |

(Continued)

FOREIGN PATENT DOCUMENTS

EP   0418791 A1   3/1991

(Continued)

OTHER PUBLICATIONS

Examiner's First Report from corresponding Australian Application No. 2004228005, dated Oct. 13, 2008.

*Primary Examiner* — Jacqueline F. Stephens
(74) *Attorney, Agent, or Firm* — Ohlandt, Greeley, Ruggiero & Perle, L.L.P.

(57) ABSTRACT

A method of forming a barrel for a tampon applicator assembly including molding a barrel then forming a rearward taper region in an area of the barrel is provided. The method includes molding a first portion of the barrel in a first mold part and a second portion of the barrel in a second mold part, the first and second mold parts meeting at a maximum outer dimension of the first portion, ejecting the barrel from the first and second mold parts, and forming a flared region in an area of the second portion.

20 Claims, 4 Drawing Sheets

U.S. PATENT DOCUMENTS

| | | | |
|---|---|---|---|
| 3,628,533 A | 12/1971 | Loyer | 604/14 |
| 3,765,416 A | 10/1973 | Werner et al. | 604/18 |
| 4,048,998 A | 9/1977 | Nigro | 604/14 |
| D250,663 S | 12/1978 | Koch et al. | D24/99 |
| 4,198,978 A | 4/1980 | Nigro | 604/14 |
| 4,361,150 A | 11/1982 | Voss | 604/15 |
| 4,421,504 A | 12/1983 | Kline | 604/12 |
| 4,428,370 A | 1/1984 | Keely | 128/838 |
| 4,508,531 A | 4/1985 | Whitehead | 604/14 |
| 4,536,178 A | 8/1985 | Lichstein et al. | 604/15 |
| 4,676,773 A | 6/1987 | Sheldon | 604/16 |
| 4,846,802 A | 7/1989 | Sanders | 604/15 |
| 4,891,042 A | 1/1990 | Melvin et al. | 604/18 |
| 4,921,474 A | 5/1990 | Suzuki et al. | 604/16 |
| 5,080,659 A | 1/1992 | Nakanishi | 604/15 |
| 5,158,535 A | 10/1992 | Paul et al. | 604/15 |
| 5,290,501 A | 3/1994 | Klesius | 264/322 |
| 5,788,663 A | 8/1998 | Igaue et al. | 604/15 |
| D415,565 S | 10/1999 | Hayes et al. | D24/141 |
| 6,045,526 A | 4/2000 | Jackson | 604/15 |
| 6,264,626 B1 | 7/2001 | Linares et al. | 604/15 |
| 6,364,854 B1 | 4/2002 | Ferrer et al. | 604/60 |
| 6,368,442 B1 | 4/2002 | Linares et al. | 156/198 |
| 6,423,025 B1 | 7/2002 | Buzot | 604/15 |
| 6,432,075 B1 | 8/2002 | Wada et al. | 604/15 |
| 6,432,076 B1 | 8/2002 | Wada et al. | 604/15 |
| 6,478,764 B1 | 11/2002 | Suga | 604/15 |
| 7,172,573 B1 | 2/2007 | Lamb | 604/59 |
| 7,727,208 B2 | 6/2010 | LeMay et al. | 604/150 |
| 2003/0105421 A1* | 6/2003 | Jarmon et al. | 604/11 |
| 2004/0199102 A1 | 10/2004 | LeMay et al. | 604/15 |

FOREIGN PATENT DOCUMENTS

| | | |
|---|---|---|
| JP | 04322647 A | 11/1992 |
| JP | 04322648 A | 11/1992 |

* cited by examiner

BARREL FOR A TAMPON APPLICATION ASSEMBLY AND METHODS OF FORMING

CROSS-REFERENCE TO RELATED APPLICATIONS

This application is a divisional of prior U.S. application Ser. No. 10/619,677, filed Jul. 15, 2003 now U.S. Pat. No. 7,704,242, which is a continuation-in-part of U.S. application Ser. No. 10/407,159, filed on Apr. 4, 2003 now abandoned. The contents of U.S. application Ser. No. 10/619,677, filed Jul. 15, 2003, and U.S. application Ser. No. 10/407,159, filed on Apr. 4, 2003, are hereby incorporated by reference.

BACKGROUND

1. Field of the Disclosure

The present disclosure is related to a barrel of a tampon applicator assembly and methods of forming such a barrel.

2. Description of Related Art

A tampon applicator assembly is used to inject an absorbent or hygienic material, known as a tampon pledget, into a vaginal cavity. Commercial tampon applicator assemblies typically have a barrel and a plunger used to expel a pledget housed in the barrel.

The use of such an assembly requires a user to grip the barrel and guide it easily into the vaginal cavity. This is particularly important since a portion or all of the assembly is out of a direct line of sight of the user during insertion. Accordingly, an assembly that is difficult to grip and control can hinder proper and comfortable delivery of the pledget.

Another problem associated with a difficult to grip and control assembly is that the user often applies excessive gripping force on the barrel to compensate for the lack of gripability. This excessive force may partially deform and/or damage the barrel and/or plunger, thereby distorting the assembly and obstructing the normal pathway of the pledget therefrom. As a result, the user may be required to apply a significant amount of force to eject the pledget from the assembly, which may result in discomfort to the user.

Many factors combine to increase the comfort of the user during the use of a tampon applicator assembly. For example, the user's comfort can be affected by one or more of ease factors, such as the ease with which: the assembly is inserted into the vagina, the pledget is expelled from the assembly, and the spent assembly is removed from the vagina. However, designing a the assembly to incorporate features that improve one or more of these areas can drastically increase the cost of manufacture of the assembly.

Thus, there is a need to provide simple, low cost methods of forming an improved tampon applicator assembly, which increase the user's comfort by addressing one or more of the aforementioned ease factors.

BRIEF SUMMARY

The present disclosure provides a method of forming a barrel of a tampon applicator assembly.

The present disclosure also provides a method of forming a barrel in which the barrel has a flared finger grip.

The present disclosure provides a method of forming a barrel having a finger grip having a shoulder region and a flared region.

The present disclosure further provides a method of forming a barrel having a tapered tip, a tapered main section, and a flared finger grip.

The present disclosure provides a method including molding a barrel then forming a flared region in an area of the barrel.

The present disclosure provides a method including: molding a first portion of the barrel in a first mold part and a second portion of the barrel in a second mold part with the first and second mold parts meeting at a maximum outer dimension of the first portion; ejecting the barrel from the first and second mold parts; and forming a flared region in an area of the second portion.

The present disclosure also provides a method including: placing a first mold cavity and a second mold cavity in fluid communication with one another with the first and second mold cavities meeting at a maximum outer dimension of the first mold cavity; injecting a material into the first and second mold cavities to form the barrel; ejecting the barrel from the first and second mold cavities; and forming a flared region in a portion of the barrel ejected from the second mold cavity.

Further, the present disclosure provides a barrel for use with a tampon applicator assembly. The barrel includes an insertion tip, a main section, and a finger grip. The finger grip has a first region, a gripping region, and a second region. The first region intersects with the main section at a first plane having a first outer dimension. The gripping region intersects with the first region and has a second outer dimension. The second region intersects with the gripping region and has a third outer dimension. The first outer dimension is larger than the second outer dimension and the third outer dimension is larger than the second outer dimension. The barrel with the exception of the second region is formed by a two-part molding operation, while the second region is formed by a forming operation after the two-part molding operation.

The above-described and other features and advantages of the present disclosure will be appreciated and understood by those skilled in the art from the following detailed description, drawings, and appended claims

DETAILED DESCRIPTION

Figure 1:
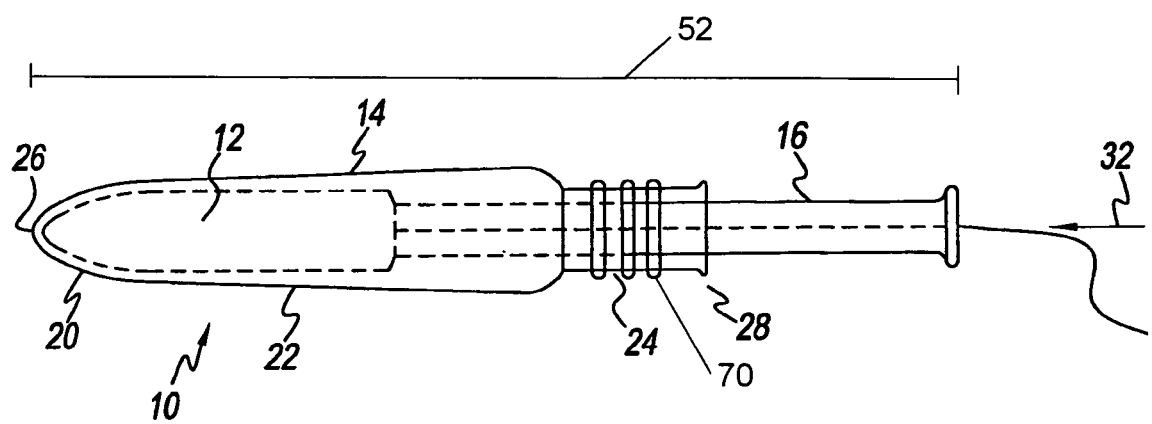
FIG. 1 is a side view of an exemplary embodiment of a tampon applicator assembly according to the present disclosure.
Figure 2:
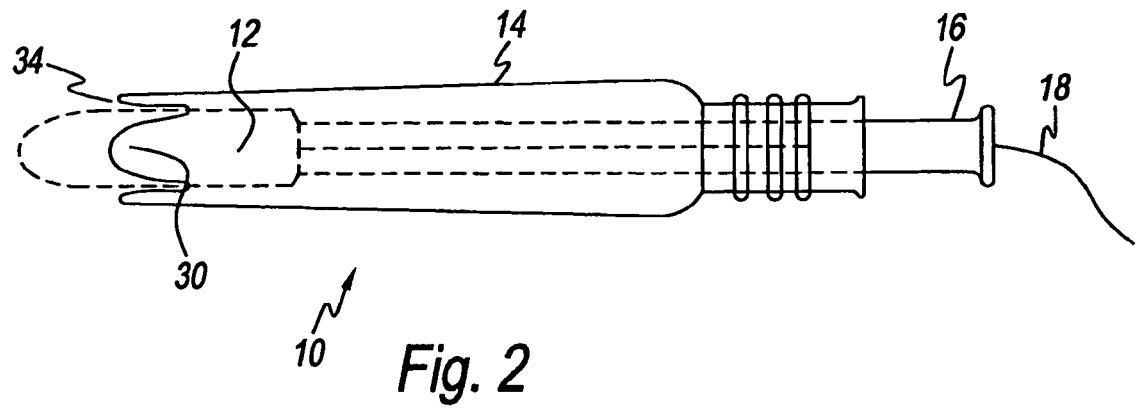
FIG. 2 is a side view of the assembly of FIG. 1 during expulsion of the pledget.

Referring now to the drawings and more particularly to FIGS. 1 and 2, an exemplary embodiment of an improved tampon applicator assembly generally represented by reference numeral 10 is illustrated. The improved assembly 10 is easier to insert, use, and remove than prior assemblies.

Assembly 10 has a pledget 12, a barrel 14, and a plunger 16. Pledget 12 is adapted to be disposed in barrel 14. Pledget 12 has a withdrawal cord 18 connected thereto, which extends through barrel 14 and plunger 16, and out of assembly 10.

Barrel 14 is sub-divided into three sections, namely an insertion tip 20, a main section 22, and a finger grip 24.

Insertion tip 20 defines a first or distal end 26 of barrel 14, while finger grip 24 terminates at a second or plunger end 28 of the barrel.

Plunger 16 is adapted to expel pledget 12 from barrel 14. For example, first end 26 can include a number or plurality of individual petals 30 disposed about the end. Petals 30 open (FIG. 2) upon application of a predetermined expulsion force by pledget 12. Plunger 16 is slidably disposed in barrel 14 at second end 28. Pledget 12 is expelled through first end 26 through the movement of plunger 16 in the direction of arrow 32. As plunger 16 moves in the direction of arrow 32, the plunger urges pledget 12 into petals 30 until the petals open and the pledget is expelled from barrel 14 through first end 26.

Petals 30 are defined in insertion tip 20 by a number or plurality of slits 34. It should be recognized that insertion tip 20 of barrel 14 is illustrated by way of example only as including four petals 30. Of course, insertion tip 20 having more or less than four petals 30 is contemplated by the present disclosure. For example, insertion tip 20 can have any number of petals, preferably between about 2 to about 6 petals, more preferably between about 3 to about 5 petals, most preferably about 4 petals.

Figure 3:
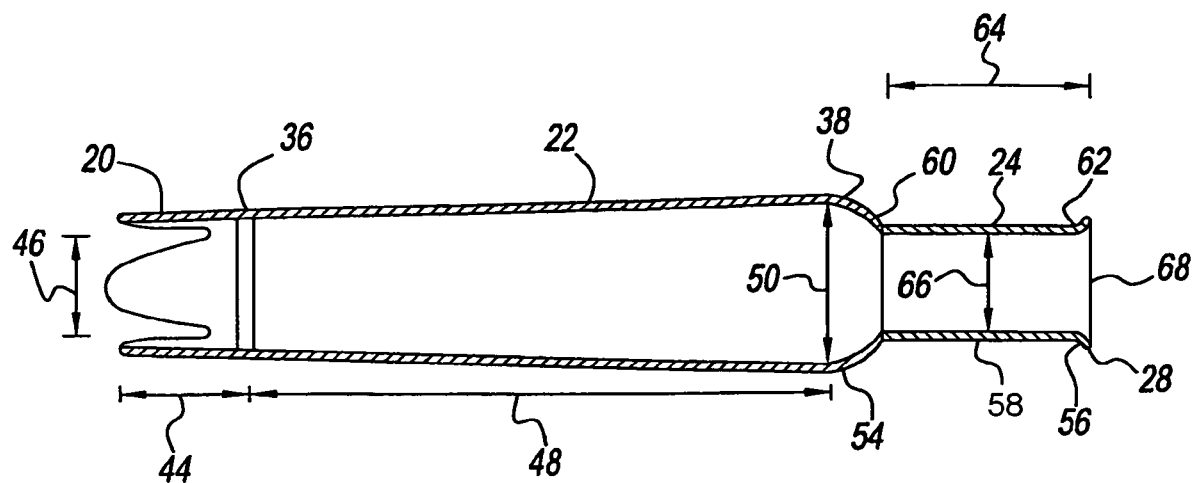
FIG. 3 is a sectional view of the barrel of FIG. 2.
Figure 4:
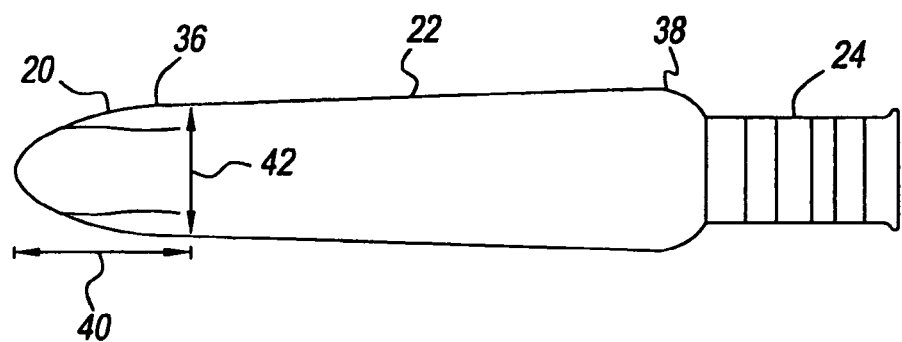
FIG. 4 is a side view of the barrel of FIG. 1.

Referring now to FIGS. 3 and 4, insertion tip 20 and main section 22 intersect at a first plane 36, while the main section and finger grip 24 intersect at a second plane 38. Second plane 38 is, preferably, defined at the point where finger grip 24 curves away from main section 22.

When in a closed position as shown in FIG. 1, petals 30 collectively provide insertion tip 20 with a shape that facilitates insertion. Through both qualitative and quantitative consumer research, it has been determined that providing insertion tip 20 with a taper greatly enhances the actual and perceived level of comfort associated with inserting barrel 14 of assembly 10.

Insertion tip 20 has a length 40 and an outer dimension 42. Assembly 10 preferably has a circular cross section such that outer dimension 42 is an outer diameter. However, it is contemplated by the present disclosure for assembly 10 to have other non-circular cross sections, such as ovoid or polygonal.

Length 40 is defined as the distance between first plane 36 and first end 26. Outer dimension 42 is tapered (e.g., decreases along length 40), linearly or non-linearly, from a maximum at first plane 36 to a minimum at first end 26. The taper of insertion tip 20 is defined as a ratio of length 40 of insertion tip 20 divided by the maximum outer dimension of the insertion tip. The maximum outer dimension of insertion tip 20 is outer dimension 42 at first plane 36. Preferably, insertion tip 20 has a taper ratio of between about 0.55 and about 1.6, more preferably more than about 0.66. For example, in a preferred embodiment insertion tip 20 has a taper ratio of between about 0.66 and about 1.6, more preferably between about 0.7 and about 0.9.

Petals 30 have a length 44 and a width 46. Insertion tip 20 has a petal length-to-width ratio, which is defined as length 44 divided by width 46. Preferably, insertion tip 20 has a petal length-to-width ratio in a range between about 0.8 to about 3.0, more preferably over about 2.0.

Further, it has been determined that providing main section 22 with a taper can also enhance the actual and perceived level of comfort associated with inserting barrel 14 of assembly 10.

Main section 22 has a length 48 and an outer dimension 50, which defines the maximum outer dimension of barrel 14. Length 48 is defined as the distance between first and second planes 36, 38. Outer dimension 50 is tapered (e.g., decreases along length 48), linearly or non-linearly, from a maximum outer dimension 50 at second plane 38 to a minimum outer dimension 42 at first plane 36.

Main section 22 has a main section taper, which is defined as a ratio of dimension 50 at second plane 38 divided by dimension 42 at first plane 36. Preferably, the main section taper has a ratio between about 1.07 to about 1.15, and more preferably between about 1.08 to about 1.13.

Barrel 14 has an overall length 52, which is defined as the distance between first and second ends 26, 28 as illustrated in FIG. 1. Second plane 38 is preferably located closer to second end 28 than to first end 26. Namely, second plane 38 and, thus, the maximum outer dimension of main section 22 (e.g., dimension 50) is located along barrel 14 more than half of overall length 52 from first end 26. Preferably, second plane 38 is located between about 55% to about 85% of overall length 52 from first end 26, more preferably between about 60% to about 75%.

This tapering of main section 22 facilitates insertion comfort by gradually parting the vulva-vaginal channel over a longer length of barrel 14 than that of only insertion tip 20. The tapering of main section 22 is, preferably, a constant taper.

It has also been determined that providing assembly 10 with finger grip 24 can enhance the actual and perceived level of comfort associated with inserting barrel 14 of assembly 10, expelling pledget 12 from the barrel, and removing the barrel.

Referring to FIG. 3, finger grip 24 is bounded by a shoulder region 54 and a flared region 56, which define a gripping region 58 therebetween. Shoulder region 54 intersects main section 22 at second plane 38 and intersects gripping region 58 at a third plane 60. Similarly, flared region 56 intersects gripping region 58 at a fourth plane 62 and terminates at second end 28.

Shoulder region 54 provides a firm grip surface during insertion of barrel 14 into the vaginal vault. Flared region 56 provides a firm grip surface during expulsion of pledget 12 from barrel 14, as well as during removal of the barrel from the body. Thus, regions 54, 56 can mitigate slipping of the user's fingers from gripping region 58.

Gripping region 58 may be concave, convex, flat, or any combinations thereof and has a length 64. Length 64 is defined as the distance between third and forth planes 60, 62. The length 64 is about 13 mm (0.5 inches) to about 25 mm (1 inch). More preferably, length 64 is about 17 mm (0.67 inches) to about 21 mm (0.83 inches), with about 19 mm (0.75 inches) being the most preferred.

Gripping region 58 has an outer dimension 66, which is substantially smaller than the outer dimension of regions 54, 56 at least at one plane along length 64. Gripping region 58 may be uniform in cross-sectional shape or area along length 64. By way of example, outer dimension 66 can be about 4.5 millimeters (mm) (0.175 inches) to about 20.5 mm (0.80 inches), more preferably about 11.5 mm (0.45 inches).

In the illustrated embodiment, shoulder region 54 has a maximum outer dimension 50 at second plane 38, while flared region 56 has a maximum outer dimension 68 at second end 28. Outer dimension 50 of shoulder region 54 may be the same as or different from outer dimension 68 of flared region 56.

Preferably, outer dimensions 50 or 68 are each larger than outer dimension 66. Outer dimension 50 is preferably about 10% to about 30% larger than outer dimension 66, more preferably about 25% larger. Further, outer dimension 68 is preferably about 10% to about 30% larger than outer dimension 66, more preferably about 15% larger.

Gripping region 58 may also have one or more gripping structures 70 to improve gripability of barrel 14. Suitable gripping structures 70 include, for example, one or more, and preferably two or more, embossments, protuberances, slits, grooves, louvers, perforations, lances, abrasive medium, high wet coefficient of friction materials, pressure sensitive adhesives, or any combinations thereof. In addition, gripping structures 70 may be formed in any shape, including, for example, arc, circle, concave, cone, convex, diamond, line, oval, polygon, rectangle, rib, square, triangle, or any combinations thereof.

Assembly 10 provides a combination of features, which achieve consumer benefits unavailable in prior assemblies. For example, assembly 10 is easily and comfortably inserted into the body. Here, the taper ratios of insertion tip 20 and main section 22 combine to gradually part the vulva-vaginal channel, while shoulder region 54 of finger grip 24 provides the user with a firm grip on barrel 14.

Additionally, assembly 10 increases the comfort of the user by providing an assembly from which pledget 12 can be easily expelled. The combination of the petal ratio, the length-to-width ratio of petals 30, and the increased outer dimensions of the ends of plunger 16 all combine to increase the ease and comfort of expelling pledget 12 from barrel 14. Further, flared region 56 of finger grip 24 provides the user with a firm grip on barrel 14 during the expulsion of the pledget 12 from the barrel.

Further, assembly 10 is easily and comfortably removed from the body. Again, the taper ratios of insertion tip 20, main section 22, as well as flared region 56 of finger grip 24 combine to increase the ease, comfort, and grip during the removal of assembly 10.

While the aforementioned configuration of barrel 14 (e.g., the taper of main section 22 and the flared region 56 of finger grip 24) improves the user's comfort, it can also lead to an increase in the cost of assembly 10.

One low cost method of making barrels for typical tampon assemblies, is to injection mold the barrel using a two-part mold. However, the configuration of barrel 14 precludes the use of two-part injection molding. The difficulty associated with two-part molding of barrel 14 having the desired configuration is illustrated with reference to FIG. 5.

During two-part molding, barrel 14 would be formed using a two-part mold 72 having a first part 74 and a second part 76. First part 74 forms a first cavity 78 having a first ejection opening 80. First cavity 78 defines a front portion 82 of barrel 14. Front portion 82 is the portion of barrel 14 from first end 26 to second plane 38. Front portion 82 begins where barrel 14 has its minimum outer dimension (e.g., first end 26) and terminates where the front portion has its maximum outer dimension (e.g., outer dimension 50). Further, front portion 82 is tapered (e.g., main section taper and insertion tip taper) from plane 38 to first end 26.

Similarly, second part 76 forms a second cavity 84 having a second ejection opening 86. Second cavity 84 defines a rear portion 88 of barrel 14. Rear portion 88 is defined as the portion from second plane 38 to second end 28. Rear portion 88 begins where barrel 14 has its maximum outer dimension (e.g., outer dimension 50), reduces to outer dimension 66 in gripping region 58, then increases again to outer dimension 68 at second end 28.

Figure 5:
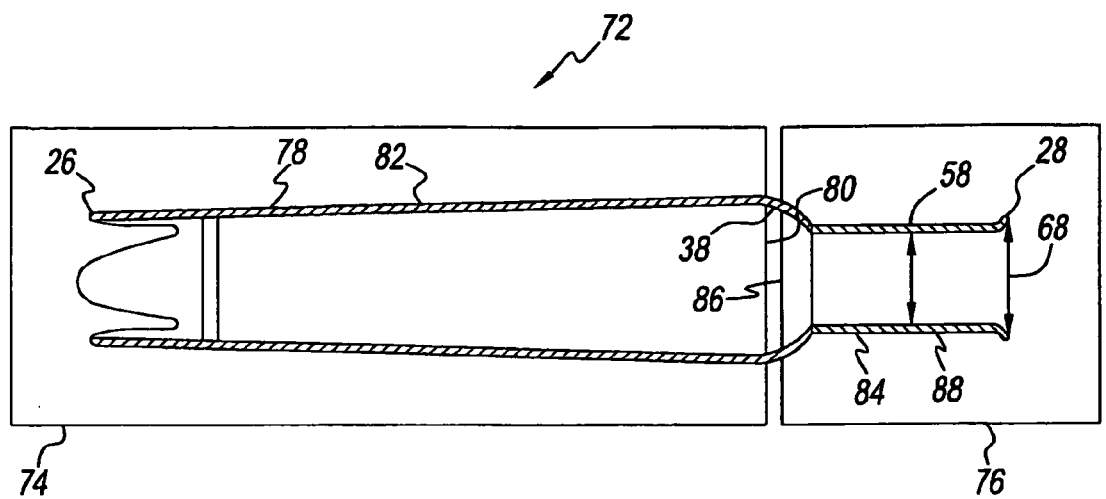
FIG. 5 is a sectional view of a molding operation for the barrel of FIG. 1 illustrating a problem overcome by the method of the present disclosure.

First and second parts 74, 76 are urged together so that first and second cavities 78, 84 are in fluid communication with one another as shown in FIG. 5. Molten material is injected into first and second cavities 78, 84, and is then cooled to form barrel 14. After molding of barrel 14, first and second parts 74, 76 are then separated so that the barrel can be ejected from mold 72 through first and second ejection openings 80, 86, respectively.

Since front portion 82 has its minimum outer dimension located at first end 26 and its maximum outer dimension at plane 38, the front portion can easily be ejected from first part 74 through first ejection opening 80. However, rear portion 88 has a larger outer dimension 68 at second end 28 than the outer dimension 66 in gripping region 58. Thus, outer dimension 68 of second end 28 prevents rear portion 88 from being easily ejected from second part 76 through second ejection opening 86.

Figure 6:
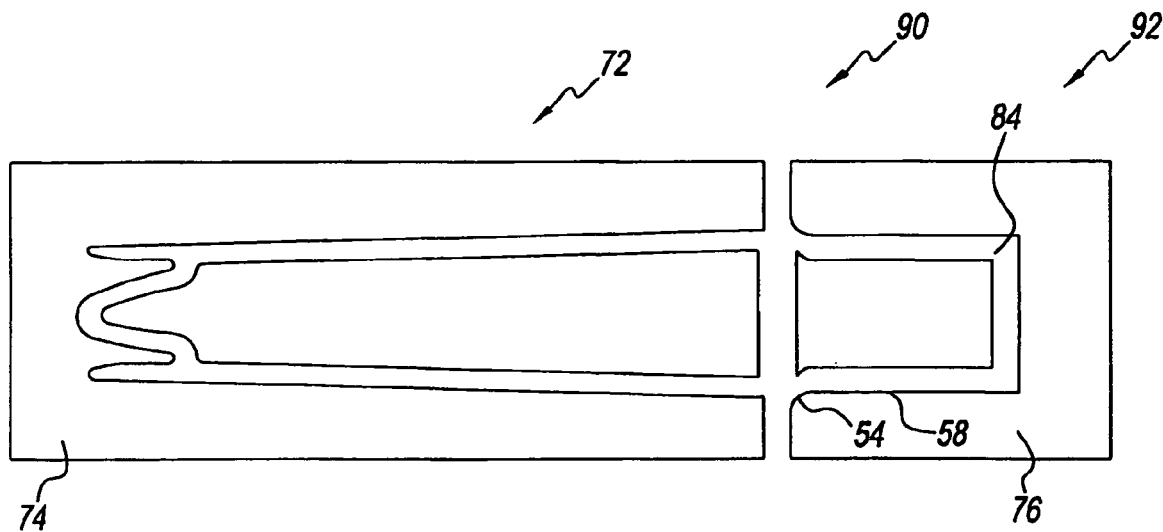
FIG. 6 is a sectional view of a molding operation according to the present disclosure.
Figure 7:
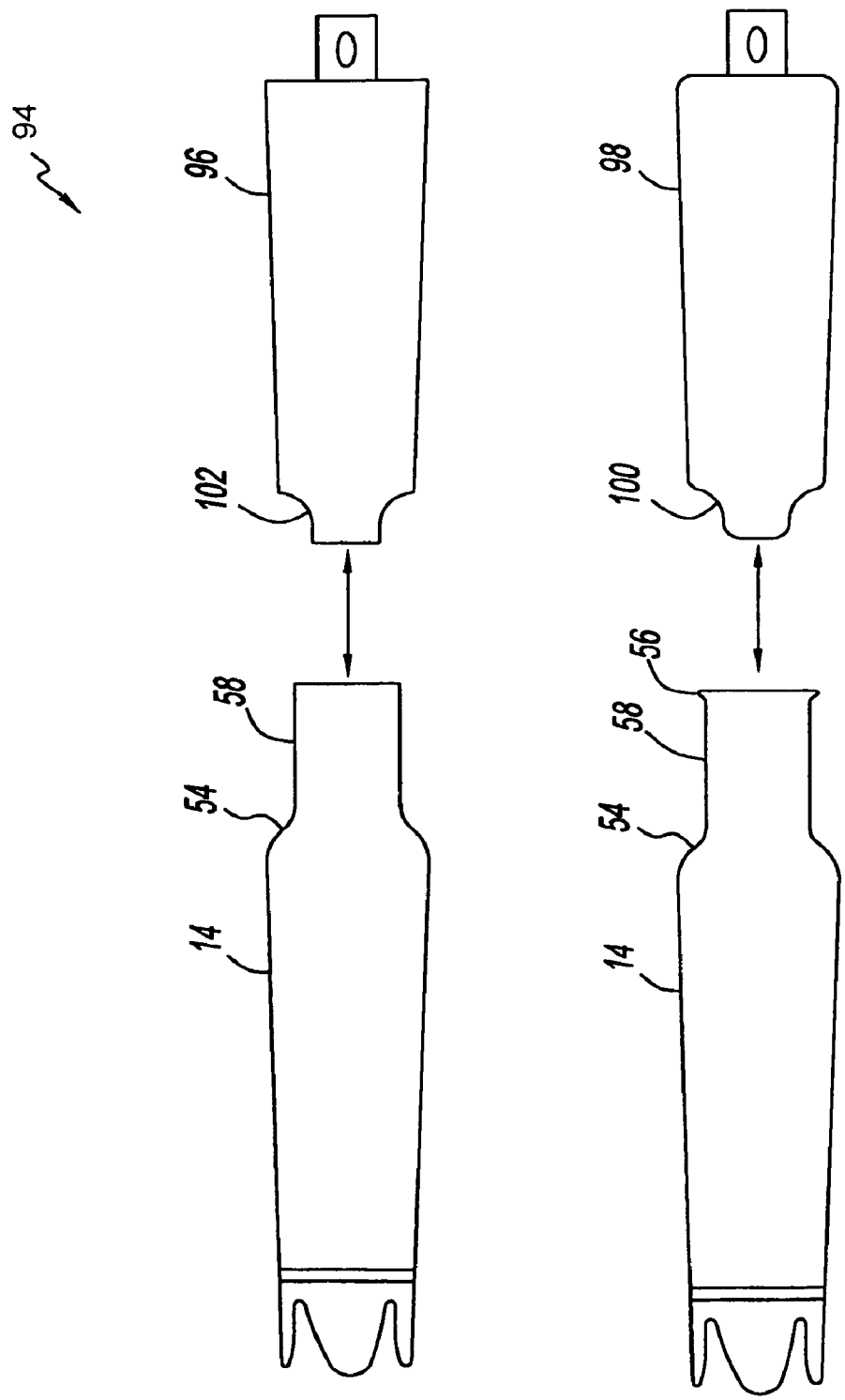
FIG. 7 is a side view of a forming operation according to the present disclosure.

An exemplary embodiment of a low cost method 90 of manufacturing barrel 14 having the desired configuration is illustrated with reference to FIGS. 6 and 7. Barrel 14 is preferably formed using a two-part molding operation 92 as in FIG. 6, followed by a post molding operation 94 as in FIG. 7. By way of example only, barrel 14 is described as being formed of low-density polyethylene (LDPE). Of course, it should be recognized that molding and forming operations 92, 94 find use with other moldable materials.

Two-part molding operation 92 uses two-part mold 72 having first part 74 and second part 76 as described in detail above with respect to FIG. 5. However, second cavity 84 defines only shoulder region 54 and gripping region 58 of barrel 14. Since rear portion 88 that is formed by second cavity 84 does not have flared region 56, it can easily be ejected from second part 76 through second ejection opening 86.

After barrel 14 is ejected from mold 72, flared region 56 is applied by forming operation 94. Forming operation 94 uses a first mandrel 96 and a second mandrel 98 to from flared region 56.

In the example where barrel 14 is formed of LDPE, first mandrel 96 is heated to about 210 degrees Fahrenheit (F) to about 230 degrees F., more preferably about 220 degrees F. First mandrel 96 is then brought into contact with second end 28 of barrel 14 for about 1 second to about 3 seconds, more preferably about 2 seconds. Since first mandrel 96 is heated to a temperature close to the melting temperature of the materials of barrel 14, the contact of the first mandrel with the barrel softens the material of the barrel.

Second mandrel 98 has a forming end 100, which is dimensioned to form flared region 56 of a desired shape in second end 28 of barrel 14. Second mandrel 98 is cooled to about 65 degrees F. to about 75 degrees F., more preferably about 70 degrees F. After first mandrel 96 is removed from second end 28, forming end 100 of second mandrel 98 is inserted into the second end. Second mandrel 98 is contacted with second end 28 of barrel 14 for about 1 second to about 3 seconds, more preferably about 2 seconds. Since forming end 100 has the desired shape of flared region 56 and has a temperature well below the melting temperature of the materials of barrel 14, the second mandrel holds the barrel in the desired shape while setting the material of the barrel.

First mandrel 96 can also have a forming end 102. Forming end 102 can have the same profile or a different profile as forming end 100 of second mandrel 96, more preferably forming end 102 has the same profile as forming end 100. Accordingly, forming end 102 of first mandrel 96 can be used to both soften and begin to re-shape second end 28 to form flared region 56. Then, forming end 100 of second mandrel 98 holds the rearward taper region in the desired shaped while the temperature of the second mandrel sets the material in the desired shape.

Preferably, the dwell time of forming operation 94 to remove first mandrel 96 and insert second mandrel 98 is between about 0.5 seconds to about 1.5 seconds, more preferably about 1 second. Thus, forming operation 94 preferably has an overall cycle time of about 2.5 seconds to about 7.5 seconds, more preferably about 5 seconds.

It has been determined that method 90 advantageously forms barrel 14 having the desired configuration without the cost and time associated with the complex molding operations as would otherwise be necessary. In addition, method 90 can be used to retrofit current manufacturing processes to simply and easily provide barrel 14 with flared region 56 on second end 28.

It should also be noted that the terms "first", "second", and "third" and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof. Therefore, it is intended that the present invention not be limited to the particular embodiment(s) disclosed as the best mode contemplated for carrying out this invention, but that the invention will include all embodiments falling within the scope of the appended claims.

What is claimed is:

1. A method of forming a barrel for a tampon applicator assembly comprising:
   molding a first portion of the barrel in a first mold part and a second portion of the barrel in a second mold part, said first and second mold parts meeting at a maximum outer dimension of said first portion;
   ejecting the barrel from said first and second mold parts; and
   forming a flared region in an area of said second portion after said barrel is ejected from said first and second mold parts.

2. The method as in claim 1, wherein forming said flared region comprises inserting a first mandrel into said area, said first mandrel having a temperature sufficient to soften said area.

3. The method as in claim 2, further comprising inserting a second mandrel into said area, said second mandrel having a shape corresponding to a desired shape of said flared region.

4. The method as in claim 3, further comprising removing said first mandrel from said area prior to inserting said second mandrel.

5. The method as in claim 3, wherein said first mandrel has a shape corresponding to said desired shape of said flared region.

6. The method as in claim 3, wherein said area receives a temperature from said second mandrel sufficient to set said area.

7. A method of forming a barrel for a tampon applicator assembly comprising:
   placing a first mold cavity and a second mold cavity in fluid communication with one another, said first and second mold cavities meeting at a maximum outer dimension of said first mold cavity;
   injecting a material into said first and second mold cavities to form the barrel;
   ejecting the barrel from said first and second mold cavities; and
   forming a flared region in a portion of the barrel ejected from said second mold cavity.

8. The method as in claim 7, wherein forming said flared region comprises heating a first mandrel to an elevated temperature, and inserting said first mandrel in said portion.

9. The method as in claim 8, wherein said elevated temperature is about 210 degrees F. to about 230 degrees F.

10. The method as in claim 8, wherein said elevated temperature is about 220 degrees F.

11. The method as in claim 8, further comprising contacting said first mandrel with said portion for about 1 second to about 3 seconds.

12. The method as in claim 11, wherein said first mandrel is contacted with said portion for about 2 seconds.

13. The method as in claim 8, wherein said first mandrel has a shape corresponding to a desired shape of said flared region.

14. The method as in claim 8, further comprising removing said first mandrel from said portion, and inserting a second mandrel in said portion, wherein said second mandrel has a shape corresponding to a desired shape of said flared region.

15. The method as in claim 14, wherein removing said first mandrel and inserting said second mandrel has a dwell time of about 0.5 seconds to about 1.5 seconds.

16. The method as in claim 15, wherein said dwell time is about 1 second.

17. The method as in claim 14, wherein said second mandrel has a reduced temperature.

18. The method as in claim 17, wherein said reduced temperature is about 65 degrees F. to about 75 degrees F.

19. The method as in claim 17, wherein said reduced temperature is about 70 degrees F.

20. The method as in claim 14, further comprising contacting said second mandrel with said portion for about 1 second to about 3 seconds.

* * * * *